United States Patent [19]

Fisher et al.

[11] Patent Number: 4,583,655

[45] Date of Patent: Apr. 22, 1986

[54] LOCKING PIN AND GUIDE MECHANISM FOR A DOOR CLOSURE

[75] Inventors: Kenneth J. Fisher, Erie; John N. Roche, Greenville, both of Pa.

[73] Assignee: American Sterilizer Company, Erie, Pa.

[21] Appl. No.: 719,905

[22] Filed: Apr. 4, 1985

[51] Int. Cl.⁴ .................................................. B65D 43/20
[52] U.S. Cl. ..................................... 220/346; 220/316
[58] Field of Search ..................... 220/316, 346, 347; 422/307; 292/21, 141, 465

[56] References Cited

U.S. PATENT DOCUMENTS

| | | | |
|---|---|---|---|
| 3,339,785 | 9/1967 | Nugent | 220/346 |
| 3,352,446 | 11/1967 | Anderson et al. | 220/346 |
| 4,082,510 | 4/1978 | Jovanovic | 220/316 |
| 4,352,439 | 10/1982 | Makhijani | 220/316 |

*Primary Examiner*—George T. Hall
*Attorney, Agent, or Firm*—Robert D. Yeager; Christine R. Ethridge

[57] ABSTRACT

A guide mechanism for use with apparatus for opening and closing a door of a chamber includes a way system for aligning the door with the chamber while the door is being opened and closed and a carriage member operatively linked to the way system for linking the door to the way system when the door is open. The carriage member includes a plurality of pins adapted to receive a portion of the apparatus when the apparatus moves the door into an open position to engage the door to the carriage member. Means are provided to coordinate the operation of the pins and the apparatus.

9 Claims, 7 Drawing Figures

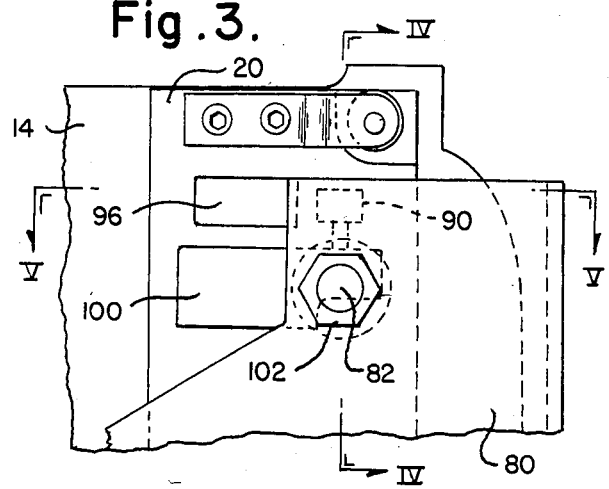
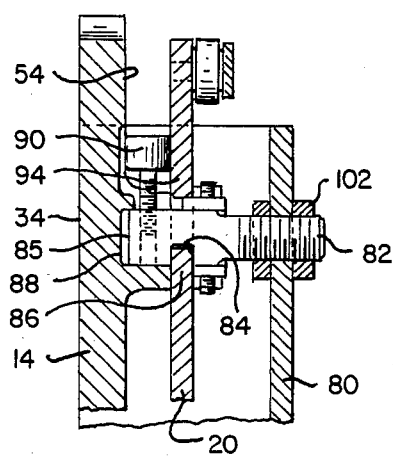
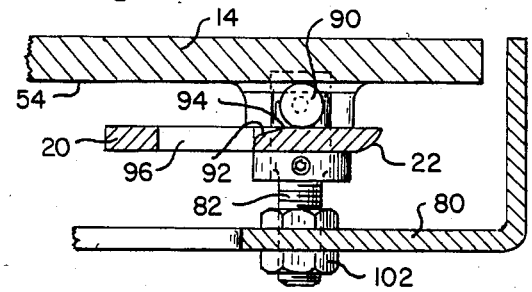
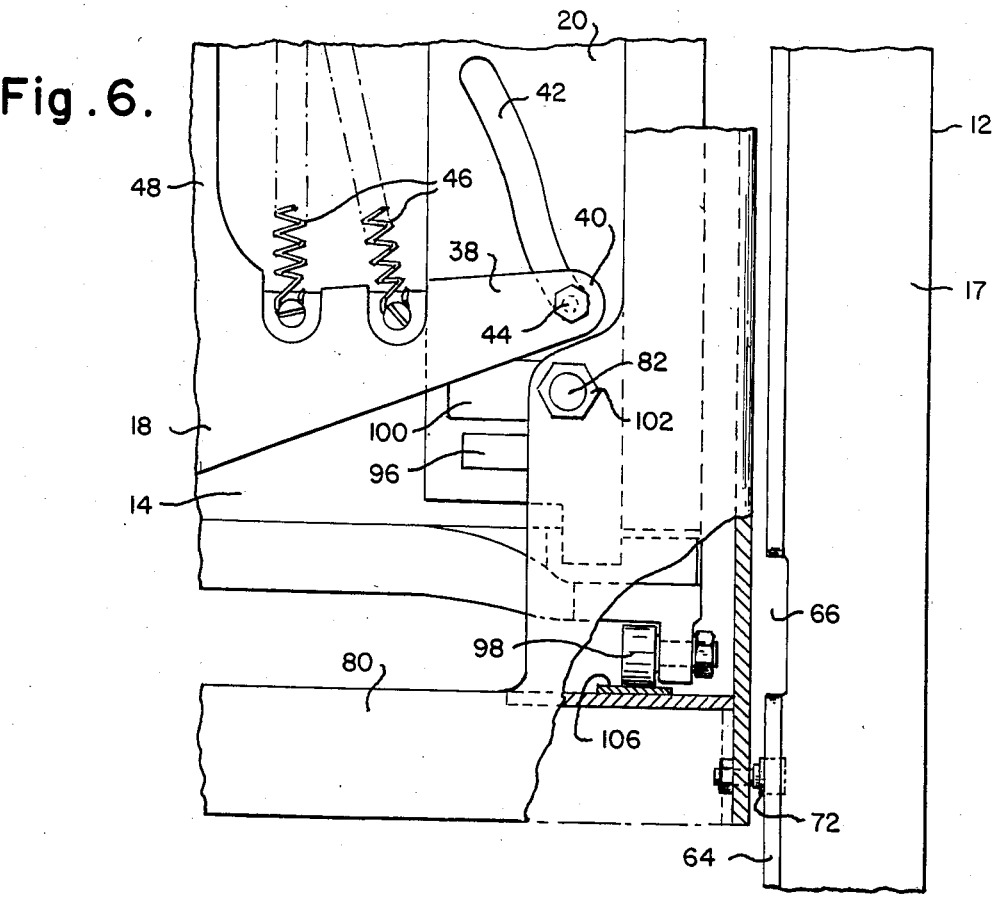

LOCKING PIN AND GUIDE MECHANISM FOR A DOOR CLOSURE

BACKGROUND OF THE INVENTION

1. Field of the Invention

The present invention relates to chamber door closures and, more particularly, to guide mechanisms for chamber door closures.

2. Description of the Prior Art

There exists a wide variety of apparatus for effecting the closure of chamber doors. For example, a sterilizer chamber that operates under pressure must have a closure which effectively seals the chamber against fluid flow. Makhijani, U.S. Pat. No. 4,352,439 which issued on Oct. 5, 1982, describes an apparatus for closing the door of a pressure chamber. The apparatus includes an operator for moving the chamber door among its closed position, its partially closed position and its open position. The apparatus also includes a movable cam member which is capable of being forced by the operator between the door and a stationary flange positioned near the chamber opening to move the door into its closed position. The Makhijani apparatus includes a guide disposed on the chamber for restricting the movement of the door to that necessary for it to travel among its three positions. The guide is a flanged member on each side of the front of the chamber. In the embodiment shown, the door slides vertically along the flanged members between its partially closed and open positions. The door moves horizontally within the limits of the flanged members between its partially closed and closed positions. In the closed position the door is held securely to the chamber by the movable cam member wedged between the door and the stationary flanged member. In the partially closed and open positions, however, the door is free to move within the horizontal limits of the flanged members, thus, permitting some play in the door as it is moved vertically between the partially closed and open positions. In these positions, the door is not secured to the chamber sufficiently to prevent such play.

In a quick closing door for a pressure chamber, like that described by the Makhijani patent, there is a need to protect the seal from unnecessary wear. Repeated rubbing against the seal which can occur due to play in the door as it is opened and closed can prematurely wear the seal. In addition, the play in the door wears against the flange members and the outer edges of the door and places uneven stress on the cable system supporting the door during movement. Further stress is placed on the cable system when the door is rotated away from the chamber to replace the seal or service the sterilizer because the weight of the door is not supported by the chamber. The play in the door as it moves between the partially closed and the open positions can hamper the ease of movement and be noisy.

There is a need, therefore, for a guide mechanism for use with an apparatus to open and close the door of a chamber. There is a further need for such a guide mechanism which will maintain the door in alignment with the chamber to prevent wear of the seal and the door and to eliminate uneven stress on a cable system holding the door.

There is a need for a mechanism which permits the door to be moved away from the chamber for servicing the seal, the chamber or the door without placing undue stress on the closure system. Finally, there is a need for a mechanism which secures the door to the chamber when the door is being opened and which permits the door to expand and contract independently of the mechanism in response to the heat and pressure changes within the chamber when the door is closed.

SUMMARY OF THE INVENTION

The present invention provides a guide mechanism for use with apparatus for opening and closing a door of a chamber. The guide mechanism includes generally a way system for maintaining the door in alignment with the chamber while the door is opened and closed, and a carriage member operatively linked to the way system for linking the door to the way system. The carriage member includes means, preferably a plurality of pin members attached to the carriage member, for engaging the door. The engaging means are so operatively associated with the apparatus that the engaging means engage the door when it is opened and disengage the door when it is closed.

A timing means may be provided for timing the operation of the egaging means with the movement of the apparatus. In the embodiment of the present invention wherein the engaging means are a plurality of pin members, each pin member is adapted to receive a portion of the apparatus therein to link the carriage member to the door. The timing means may be a timing member, preferably a roller, attached to each pin member and adapted to be moved along a path, preferably a ramp, on the apparatus to coordinate the engagement and disengagement of the pin member and the apparatus with the opening and closing, respectively, of the door. The roller is preferably moved by the movement of the apparatus. The movement of the roller moves the attached pin member into a position for receiving the portion of the apparatus when the door is opened.

The way system preferably includes a shaft attached to one side of the chamber and a track along the opposing side of the chamber. The carriage member is slidably and rotatably attached to the shaft. The carriage member preferably includes at least one roller adapted to move along the track when the carriage member slides along the shaft. The track may include at least one notch through which the roller may exit the track when the carriage member rotates about the shaft.

BRIEF DESCRIPTION OF THE DRAWINGS

The present invention can be better understood by reference to the attached drawings in which:

FIG. 3 is a partial front view of the upper right side of the carriage member and door of FIG. 1;

FIG. 4 is a partial section view of the carriage member and door taken through line IV—IV of FIG. 3;

FIG. 5 is a partial section view of the carriage member and door taken through line V—V of FIG. 3;

FIG. 6 is a partial front view of the lower right side of the carriage member and way system of FIG. 1.

DETAILED DESCRIPTION OF THE PREFERRED EMBODIMENT

FIGS. 1 through 7 illustrate the preferred embodiment of the locking pin and guide mechanism 10 of the present invention. While the guide mechanism of the present invention can be used with a variety of apparatus for opening and closing the door of a chamber, it is described herein in terms of its use with a pressure chamber, door and closure apparatus very similar to the chamber, door and closure apparatus described in Makhijani, U.S. Pat. No. 4,352,439 (the Makhijani patent). To the extent that particular features of the door and closure apparatus not necessary to the description of the guide mechanism 10 are not specifically detailed herein, reference can be made to the Makhijani patent for further teachings.

The guide mechanism 10 includes generally a way system 60 for maintaining the door of a pressure chamber in alignment with the chamber while the door is opened and closed, and a carriage member 80 operatively linked to the way system 60 for linking the door to the way system when the door is not closed.

Figure 1:
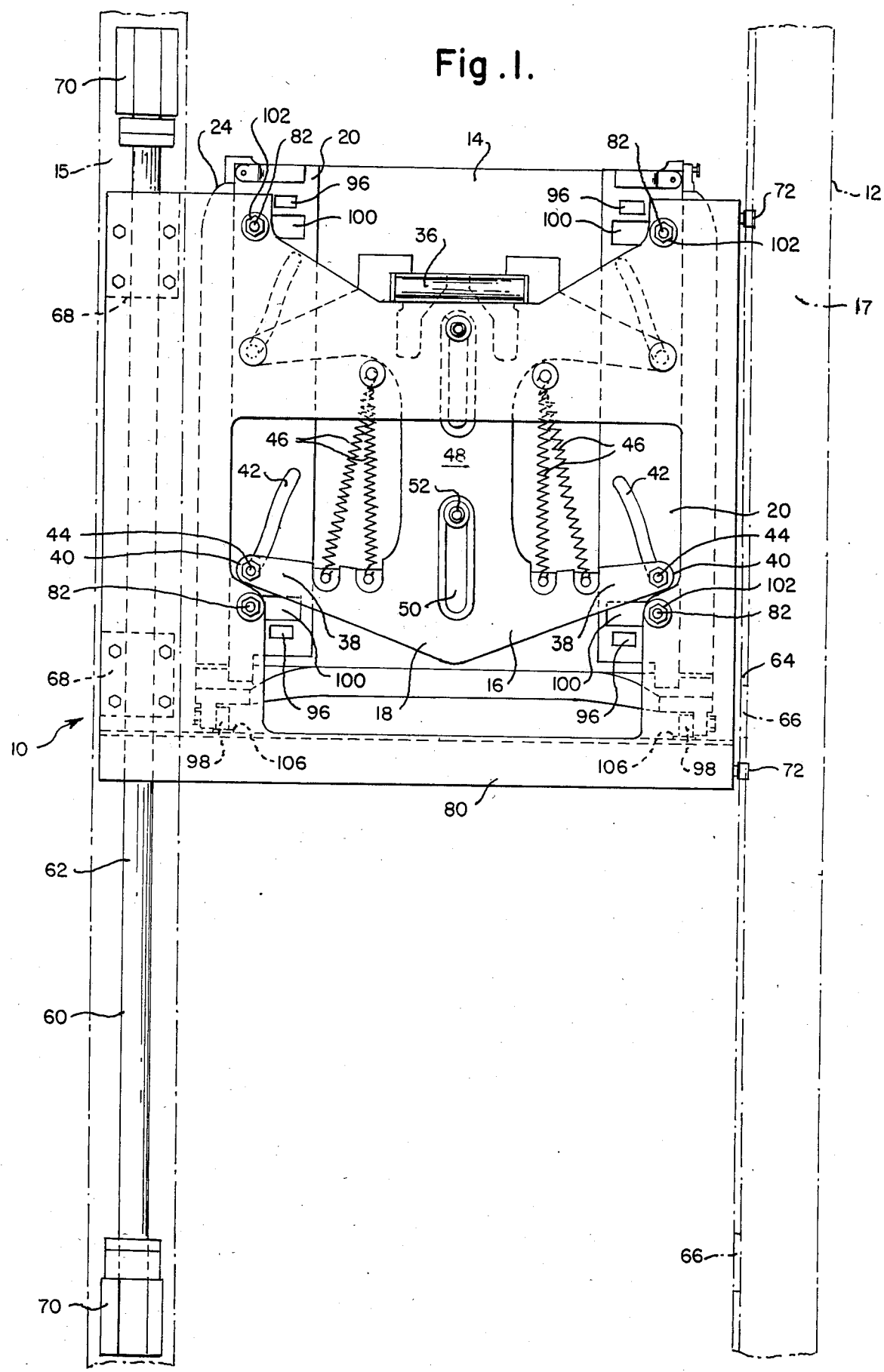
FIG. 1 is front elevation view of the preferred embodiment of the carriage member and way system of the present invention connected to a partial view of a sterilizer and door.
Figure 2:
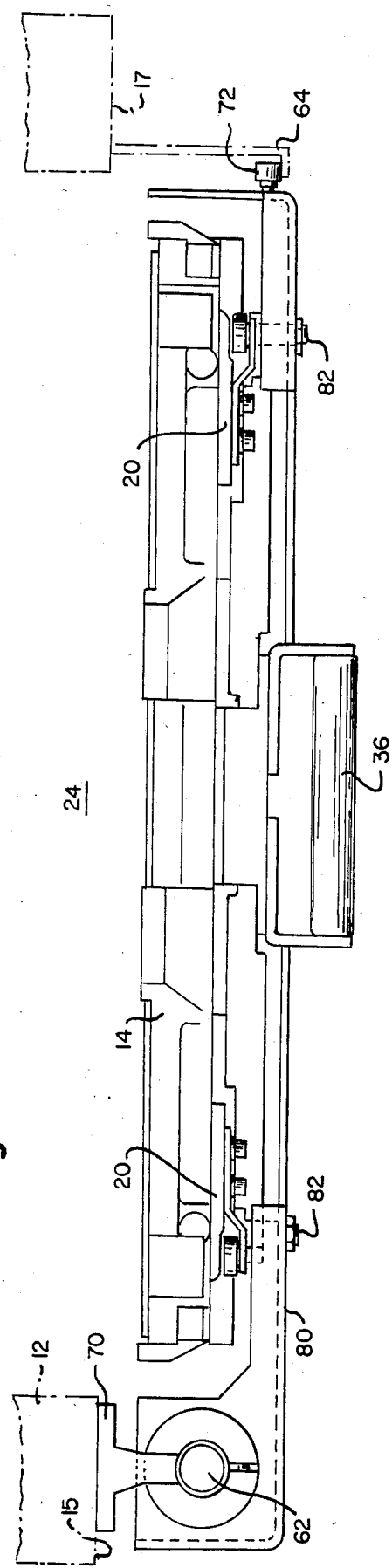
FIG. 2 is a top plan view of the carriage member, way system and door of FIG. 1.
Figure 7:
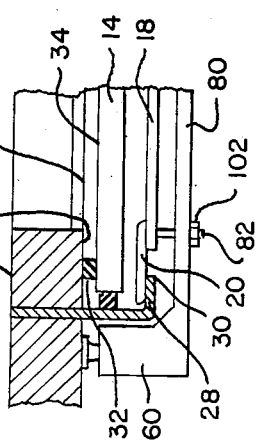
FIG. 7 is a partial section view of the flange member of a sterilizer in engagement with the cam member.

A sterilizer is shown in FIG. 1 which includes a pressure chamber 12 having an opening 24 and a door 14. The door 14 can assume any of three positions relative to the opening 24 of chamber 12: a closed position in which access to chamber 12 can not be had; a partially closed position in which door 14 confronts opening 24 but is spaced from it; and a fully open position in which the door 14 does not confront opening 24 so that access to chamber 12 is possible. Reference should be made to the Makhijani patent for views of the positions of the door. FIG. 1 shows the door in the partially closed position.

Apparatus 16 is used to move door 14 among its three positions. Apparatus 16 includes operator 18 which has a handle 36, a central portion 48 and extensions 38. Ends 40 of extensions 38 are mounted with bearings 44 within curved cam openings 42 of a movable cam member 20. Center portion 48 of operator 18 is slidably secured to outer surface 54 of door 14 by bearings attached to posts 52 of door 14 and disposed within slots 50 of center portion 48. Operator 18 can be moved vertically relative to door 14 a distance permitted by cam openings 42 and slots 50. When bearings 44 are moved upwardly to the top of cam openings 42 and the posts 52 move to the bottom of slots 50, the door 14 is moved into its closed position. Tension springs 46 counterbalance the weight of operator 18 to permit easy movement of operator 18 relative to door 14.

There are two movable cam members 20, one disposed along the length of each side of door 14. The radiused edge 22 of each cam member 20 slides against the radiused edge 30 of each stationary flanged member 28 when cam members 20 are forced outwardly relative to the center of operator 18 between flanged member 28 and door 14 by the movement of bearings 44 on ends 40 of operator 18 upwardly through cam openings 42. When the edges of cam members 20 are wedged between door 14 and flanged member 28, the interior 34 of door 14 is pushed against the seal 32 surrounding the perimeter 26 of chamber opening 24, thus moving the door 14 into its closed position.

By pulling downwardly on handle 36 of operator 18, bearings 44 are drawn downwardly through cam openings 42, forcing cam members 20 inwardly relative to the center of operator 18, out of the wedged position between door 14 and flanged member 28. Door 14 is no longer forced against seal 32 and perimeter 26 but remains in a confronting spaced relationship relative to opening 24, the partially closed position. Door 14 moves horizontally within the limits of the space between the perimeter 26 on chamber 12 and the edge 30 of flanged member 28 when door 14 moves between the closed and partially closed positions.

By pulling down further on handle 36, operator 18 pulls door 14 vertically to the fully open position. The reverse operation moves door 14 from the open position to the partially closed position, then to the closed position.

The guide mechanism 10 of the present invention permits the door 14 to be linked to the chamber by means of the way system 60 during the movement between the partially closed and open positions described above. The linkage stabilizes the position of the door 14 at a fixed position within the horizontal limits of flanged member 28.

The way system includes a shaft 62 attached by means of supports 70 to one side 15 of the front of chamber 12 and a track 64 attached to the opposing side 17 of the front of chamber 12. Track 64 includes two notches 66.

Shaft 62 includes two pillow blocks 68 to slidably and rotatably connect the carriage member 80 to shaft 62. Carriage member 80 includes two rollers 72 which travel along track 64 when carriage member 80 slides along shaft 62. The rollers 72 are sized to exit track 64 through notches 66 when carriage member 80 is rotated about shaft 62. The shaft 62 supports the linear motion of the door 14 and the overhung weight of the door 14 through the pillow blocks 68.

Carriage member 80 includes four pins 82 for engaging the apparatus 16 and thereby, door 14, when the door 14 is in the partially closed and open positions. The pins 82 extend outwardly from the door 14, through openings 10 in cam members 20 to the carriage member 80. Nuts 102 secure pins 82 to carriage member 80. Each pin 82 includes a groove 84 for receiving a portion 86 of the cam member 20 to effect the engagement. Referring to FIG. 4, the door 14 is adapted by suitably machining to receive the ends 85 of the pins 82 into a barrel section 88. The portion 86 of cam member 20 slides over the barrels 88.

A timing member for coordinating the operation of the pins 82 with the cam members 20 is also provided. A roller 90 extends laterally from each pin 82 for cooperation with a path of the cam member 20. The cam members 20 include ramps 92 cut into surfaces 94 along which the rollers 90 are moved by the lateral movement of the cam members 20 by operator 18.

The rollers 90 follow the action of the cam members 20. When the door is moved into the closed position each roller 90 falls into a space 96 on cam members 20. The cam members 20 are wedged between flanged members 28 and door 14 and the portions 86 are withdrawn from the grooves 84 in pins 82. The door 14 is securely held to the chamber 12 by the wedging action of the flanged members 28 and cam members 20.

By disengaging the pins 82 from the door 14 when it is in its closed position, the door 14 can expand and contract independently of the guide mechanism 10 as needed in response to temperature and pressure variations within the chamber 12.

When the door is moved into its partially closed position from the closed position, the operator 18 pulls the cam members 20 inwardly. As the cam members 20 are drawn laterally inwards the rollers 90 are moved up a ramp 92 onto surface 94 of the cam members 20, thereby drawing the attached pins 82 into a position for receiving the portion 86 of cam members 20. The door 14 is pulled back away from opening 24 by the motion of the roller 90 up ramp 92. When the pins 82 thus engage the cam members 20, the door 14, by means of its connection to cam members 20 and operator 18 is secured to the carriage member 80. The carriage member 80 is in turn secured to the way system 60 through shaft 62 and track 64 to secure the door 14 to the chamber. The horizontal spaced position of the door 14 relative to opening 24 and chamber 12 is fixed.

The door 14 can then be moved downwards vertically by means of operator 18 to the open position. The fixed position of the door 14 due to the engagement of pins 82 and cam member 20 and the linkage to the way system 60 through carriage member 80 maintains the door 14 in alignment with the chamber 12 during movement between the partially closed and open positions. Any play in the door is eliminated, along with the consequent wear on the seal 32, flanged member edges 30 and door 14.

The carriage member 80 also includes two wear plates 106 to support two rollers 98 on the door 14. The weight of the door 14 is thus supported by the carriage member 80 rather than pins 82. The carriage member 80 is in turn supported, through the way system 60, by chamber 12. The rollers 98 can roll on the wear plates 106 to provide a frictionless motion to the door's horizontal motion relative to opening 24 when moving between the closed and partially closed positions.

What is claimed is:

1. A guide mechanism for use with apparatus for opening and closing a door of a chamber comprising:
   a way system for maintaining the door in alignment with the chamber while the door is opened and closed; and
   a carriage member operatively linked to the way system for linking the door to the way system, the carriage member having means for engaging the door, the engaging means being so operatively associated with the apparatus that the engaging means engage the door when it is opened and disengage the door when it is closed.

2. A guide mechanism as recited in claim 1 further comprising means for timing the operation of the engaging means with the movement of the apparatus.

3. A guide mechanism as recited in claim 1 wherein the way system comprises:
   a shaft connected to one side of the chamber; and
   a track connected to the opposing side of the chamber, the track having at least one notch therein;
   the carriage member being slidably and rotatably attached to the shaft and having at least one roller adapted to run along the track when the carriage member slides along the shaft, the roller being adapted to exit the track through the notch when the carriage member is rotated about the shaft.

4. A guide member as recited in claim 1 wherein the engaging means are a plurality of pin members connected to the carriage member, each pin member being adapted to receive a portion of the apparatus therein to link the carriage member to the door.

5. A guide mechanism as recited in claim 4 further comprising a timing member attached to each pin member, the timing member being adapted to move along a path in the apparatus to coordinate the engagement and disengagement of the pin member and the portion of the apparatus with the opening and closing, respectively, of the door.

6. A guide member as recited in claim 5 wherein the timing member is a roller and the path is a ramp along which the roller is forced for moving the attached pin member into a position for receiving the portion of the apparatus when the apparatus opens the door.

7. A guide mechanism for use with apparatus for closing a door of a chamber, the chamber having a stationary member spaced from a chamber opening, and the apparatus having an operator for moving the door among an open position, a partially closed position in which the door confronts the chamber opening and a closed position in which the door seals the chamber opening, and a movable member adapted to be forced by the operator between the door and the stationary member to move the door into its closed position, the guide mechanism comprising:
   a way system for maintaining the door in alignment with the chamber while the door is moved between its partially closed and open positions; and
   a carriage member operatively linked to the way system for linking the door to the way system, the carriage member having means for engaging the door, the engaging means being so operativley associated with the movable member that the engaging means engage the door when it is moved into its partially closed and open positions, and disengage the door when it is moved into its closed position.

8. A guide mechanism as recited in claim 7 wherein the way system comprises:
   a shaft connected to one side of the chamber, the carriage member being slidably and rotatably connected to the shaft; and
   a track connected to the opposing side of the chamber, the track having at least one notch therein, the carriage member having at least one roller adapted to move along the track when the carriage member slides along the shaft and adapted to exit the track through the notch when the carriage member rotates about the shaft.

9. A guide member as recited in claim 7 wherein the engaging means are a plurality of pin members connected to the carriage member, each pin member being adapted to receive a portion of the movable member therein to link the carriage member to the door, each pin member having a roller member attached thereto, and each roller member being adapted to be moved along a ramp on the movable member when the movable member is moved to move the pin member into a position for receiving the portion of the movable member.

* * * * *

UNITED STATES PATENT AND TRADEMARK OFFICE
CERTIFICATE OF CORRECTION

PATENT NO. : 4,583,655
DATED : April 22, 1986
INVENTOR(S) : John N. Roche and Kenneth J. Fisher It is certified that error appears in the above—identified patent and that said Letters Patent is hereby corrected as shown below:

Col. 2, line 23, delete "egaging" and substitute therefor --engaging--;

Col 4, line 39, delete "10" and substitute therefor --100--;

Col. 4, line 43, delete "suitably" and substitute therefor --suitable--; and,

Col. 6, line 33, delete "operativley" and substitute therefor --operatively--.

Signed and Sealed this

Second Day of September 1986

[SEAL]

Attest:

Attesting Officer

DONALD J. QUIGG

Commissioner of Patents and Trademarks